United States Patent [19]

Metz et al.

[11] 4,008,324
[45] Feb. 15, 1977

[54] PHENOXYALKYLCARBOXYLIC ACID SALT OF 1-CINNAMYL-4-DIPHENYLMETHYL PIPERAZINE, METHOD OF PREPARATION AND ANTIHYPERCHOLESTEREMIC

[75] Inventors: Gunter Metz, Blaubeuren; Manfred Specker, Ehingen (Danube), both of Germany

[73] Assignee: Ludwig Merckle KG, Blaubeuren, Germany

[22] Filed: Jan. 20, 1976

[21] Appl. No.: 651,284

[30] Foreign Application Priority Data

Jan. 23, 1975 Germany .......................... 2502679

[52] U.S. Cl. ............................ 424/250; 260/240 K
[51] Int. Cl.[2] ............. C07D 295/00; A61K 31/495
[58] Field of Search .................. 260/240 R, 240 K; 424/250

[56] References Cited

UNITED STATES PATENTS

| | | | |
|---|---|---|---|
| 2,882,271 | 4/1959 | Janssen | 260/240 K UX |
| 3,288,795 | 11/1966 | Irikura et al. | 424/250 X |
| 3,631,038 | 12/1971 | Reicheneder et al. | 424/250 X |
| 3,773,939 | 11/1973 | Janssen | 260/240 K X |

*Primary Examiner*—Allen B. Curtis
*Attorney, Agent, or Firm*—Haseltine, Lake & Waters

[57] ABSTRACT

Salts of 1-cinnamyl-4-diphenylmethyl piperazine and their method of preparation of compositions thereof is described. These compounds have antihypercholesteremic activity.

3 Claims, No Drawings

PHENOXYALKYLCARBOXYLIC ACID SALT OF 1-CINNAMYL-4-DIPHENYLMETHYL PIPERAZINE, METHOD OF PREPARATION AND ANTIHYPERCHOLESTEREMIC

The invention is concerned with new phenoxyalkylcarboxylic acid derivatives, particularly halophenoxyalkylcarboxylic acid salts of 1-cinnamyl-4-di-phenylmethylpiperazine (cinnarizine), which can be expressed by the following structural formula:

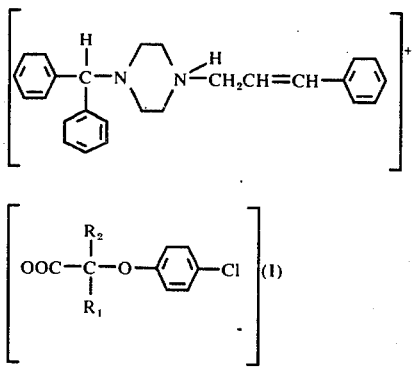

wherein $R_1$ is a hydrogen atom, a low alkyl group of 1 to 4 carbon atoms or a further p-chlorophenoxy group, and $R_2$ is a hydrogen atom or a low alkyl group of from 1 to 4 carbon atoms.

The expression "a low alkyl group" covers alkyl groups having 1–4 carbon atoms, in particular the methyl, ethyl, propyl and isopropyl groups.

As numerous investigations have shown, p-chlorophenoxyacetic acid, p-chlorophenoxypropionic acid, p-chlorophenoxyisobutyric acid and bis-(p-chlorophenoxy) acetic acid, as well as the esters and amides thereof have a generally lipid-reducing action.

As representatives of these compounds which are best known medically are 2-(p-chlorophenoxy)-2-methylpropionic acid-ethylester (clofibrate), and the corresponding carboxylic acid (clofibrinic acid).

Since clofibrate, an ester, only develops its lipid-reducing action after hydrolysis to form clofibrinic acid, this acid should also be considered as illustrating the actual principle upon which the action is based. However some disadvantages, e.g. the unpleasant odor and an irritant effect on the gastro-intestinal tract, inherent in the acid, stand in the way of the therapeutical use of clofibrinic acid.

To overcome these objections, organic basic salts (German Patent Specification OS No. 1,960,273) and inorganic basic salts, e.g. aluminum salts (German Patent Specification OS No. 1,767,533) have been produced.

Furthermore, various pharmacological tests on animals have shown that clofibrinic acid, administered orally, leads to appreciable reduction of serum-chloesterol and serum-triglyceride values only when a normal diet is taken, whereas when additional cholesterol and cholic acid are administered, i.e., when a fat diet is taken, no pronounced lipoid reduction can be achieved upon administration of clofibrinic acid.

As more recent investigations have shown, this is due to the fact that clofibrinic acid intervenes in an inhibitive manner in the endogenous hepatic metabolism exclusively, but when fats and cholesterol are administered exogenously, such activity cannot develop.

Surprisingly, it has been found that salts of cinnarizine with phenoxyalkylcarboxylic acids exhibit a synergistic effect, which is manifested by activity which exceeds the effect of the individual compounds. Thus, for example, in tests on animals, the salt of cinnarizine with clofibrinic acid exhibits a greater activity not only when a normal diet is taken but also when cholesterol loading occurs.

Cinnarizine itself is a well-known compound with anti-histaminic and cerebral and peripheral vasodilatory effects. A lipid-effect, peculiar to cinnarizine, has not previously been described.

On the other hand it is known that similar diarylalkylpiperazines, such as chlorcyclizine exhibited lipid-reducing properties in tests on animals, and particularly high serum-cholesterol values could be reduced (Toxicol. and Appl. Pharmacol. 7, 257, 1965).

In this study it was possible to show that, in the lipid and cholesterol synthesis, only the $C^{14}$-acetate inclusion was raised and not the $C^{14}$-mevalonate inclusion, a precursor to cholesterol biosynthesis.

The compounds in accordance with the invention exhibit very low toxicity compared with clofibrate and clofibrinic acid. For example, the acute oral toxicity of the compound of Example 1 is >1.5 g/kg in the mouse, and 6.81 g/kg in the rat. According to German Patent Specification OS 21 61 739 however, the oral $LD_{50}$ of clofibrate is 1.285 g/kg (mouse) and 1.65 g/kg (rat), and that of clofibrinic acid is 1.17 g/kg (mouse) and 1.25 g/kg (rat). The toxicity of cinnarizine in the mouse is given as >1280 mg/kg. The anti-lipemic effectiveness of the compound of the invention, as indicated hereinafter in Example 1, was tested on female rats against the known anti-lipemic agent, clofibrate and clofibrinic acid.

In a first series, effectiveness on normo-lipemic rats (body weight 60 – 95 g) was investigated, the animals receiving a standardized, laboratory diet in pellet form (normal diet) over the entire 14-day test period. The diet consisted mainly of raw proteins and carbohydrates with a raw fat content of 3.9% max., enriched with vitamins, mineral substances and amino acids.

The compounds and the vehicle (1% tragacanth solution) were administered daily by means of a throat bougie. Twenty-four hours after the last administration, blood samples were taken for determining the serum-cholesterol and serum-triglyceride levels. In a further study, effectiveness in rats with hypercholesteremia was investigated using the procedure published by Berger et al., Proc Soc. Exp. Biol. 132, 293 (1969).

For inducing artificial hypercholesteremia, the initially normolipemic animals were given the above-described standardized laboratory diet in pulverized form which was mixed with 2% cholesterol and 1% cholic acid. (Hypercholesterol diet).

The results of these two series are given in Table 1. The statistical significance, $p$, of the results is also given.

For the purpose of further measuring the anti-lipemic activity values, the compound as stated hereinafter in Example 1 was tested on the hyperlipemic rat (female and male animals with a body weight of 120 to 140 g), the test conditions being a modified adaptation of those used in an investigation carried out by Timms et al., Biochem. Pharmacol. 18, 1861, (1969).

In these tests the animals were fed a fat diet of the following composition over a period of 3 weeks:

| | |
|---|---|
| Casein | 12% |
| Saccharose | 10% |
| Starch | 24.8% |
| Cellulose | 1.0% |
| Mineral mixture | 6.0% |
| Vitamin mixture | 1.0% |
| Cholesterol | 5.0% |
| Choline chloride | 0.2% |
| Butter-fat (oral) | 20.0% |
| Butter-fat (mixed in) | 20.0% |

After the third week of the tests the animals were each given, over a period of 10 days, 125 mg/kg of the compound of Example 2 as an admixture to the fat diet. Examinations of the blood to determine the serum-cholesterol and serum-triglyceride levels were carried out after 0.21 and 35 days.

As control values, use can be made of the results of a very similar investigation of the substance 2-(p-chlorophenoxy)-2-methyl-propionic acid-[2-(nicotinoyloxy)-ethyl]-ester (etofibrate), and of a mixture of doses of 150 mg/kg clofibrate and 80 mg/kg nicotinic acid, which doses are equimolar to the above-mentioned substance; the results referred to above were published in Arzneim.-Forsch. 24, 1990 (1974).

In this study the animals were given the same fat diet for 14 days as a preliminary, and then received the compounds etofibrate as well as clofibrate and nicotinic acid as admixtures to the fat diet.

Despite the different time sequences, comparison of the test results is permissible, since the five-week study for measuring the values obtained with the compound of Example 2 was carried out using considerably sharper criteria.

The results of this study are shown in Table 2 as well as those of the above-mentioned study published in Arzneimittel-Forschung.

As the results show, a considerable significant rise in the cholesterol and triglyceride value occurs when the fat diet is taken. Compared with the results obtained in the tests using etofibrate, as well as clofibrate-nicotinic acid, which in the amounts administered had no effect whatsoever, the compound of Example 1 results in a sharp reduction in triglycerides and a pronounced slowing effect upon the cholesterol level.

The triglyceride level, recorded after 3 weeks, fell by 15.9% compared with the 30% drop for the control group, giving a significance of $p > 0.05$. The cholesterol level after 5 weeks corresponds to the initial value (−0.6%) after 3 weeks, and compared with the control group a drop of 6.7% is achieved.

Thus the results obtained in the three series of tests correspond to the values given in the literature on the subject, according to which clofibrate and clofibrinic acid are alone able to influence the endogenous metabolism, whereas in the case of a diet containing cholesterol and fat, no anti-lipemic effect can be measured.

Thus the compound of Example 1 differs considerably from the known properties of clofibrate and clofibrinic acid, the pharmacological results obtained indicating that, in addition to increased effectiveness with low toxicity, an increased therapeutical index may also be expected. This can also be seen from the fact that 18.5 mg/kg of clofibrinic acid correspond to a test dose of 50 mg/kg of the compound of Example 1, and 46 mg/kg of clofibrinic acid correspond to a test dose of 125 mg/kg. of that compound.

Table 1

| Compound | mg/kg | Normal diet | | | | Hypercholesterol diet | | | |
|---|---|---|---|---|---|---|---|---|---|
| | | Cholesterol mg/% | Reduction % | Triglycerides mg % | Reduction % | Cholesterol mg % | Reduction % | Triglycerides mg % | Reduction % |
| Control | — | 93.8 | — | 87.0 | — | 318.9 | — | 86.0 | — |
| Example 2 | 50 | 88.1 | −6.1 | 81.8 | −6.0 | 305.0 | −4.4 | 80.3 | −6.6 |
| | 125 | 96.5 | — | 65.8* | −24.4 | 288.6 | −9.5 | 70.9* | −17.6 |
| Control | — | 76.9 | — | 123.8 | — | 358.6 | — | 86.4 | — |
| Clofibrate | 250 | 56.1*** | 27.0 | 66.5*** | 46.3 | 347.9 | 3.0 | 75.6 | 12.5 |
| Control | — | 95.7 | — | 69.1 | — | 536.6 | — | 75.9 | — |
| Clofibrinic acid | 100 | 96.9 | — | 54.8 | 20.7 | 572.8 | — | 69.7 | 8.2 |
| | 250 | 89.4 | 6.6 | 50.8* | 26.5 | 587.8 | — | 62.7 | 17.4 |

*p <0.05
***p <0.001

Table 2

| Compound | mg/kg | Cholesterol (mg %) | | | | Triglycerides (mg %) | | | |
|---|---|---|---|---|---|---|---|---|---|
| | | Initial value | after 3 weeks | | after 5 weeks | | Initial value | after 3 weeks | | after 5 weeks | |
| | | | % | 1) | % | 2) | | % | 1) | % | 2) |
| Control I 3) | — | 55.6 | 50.4 | −9.4 | 56.3 | +11.7 | 69.9 | 107.7 | +54.1 | 99.5 | −7.6 |
| Control II 4) | — | 50.1 | 78.8 | +57.3 | 118.3 | +50.1 | 70.6 | 181.9 | +157.6 | 204.0 | +12.1 |
| Example 1 | 125 | | 109.8 | | 109.2 | −0.6 | | 169.8 | | 142.8 | −15.9 |

1) percentage change from initial value
2) percentage change from value after 3 weeks
3) Control group normal diet
4) control group fat diet
Comparative values from Arzneim.-Forschung 24, 1990 (1974)

| | Cholesterol (mg %) | | Triglycerides (mg %) | |
|---|---|---|---|---|
| Initial | after 2 weeks | after 3 weeks | Initial | after 2 weeks | after 3 weeks |

Table 2-continued

| Compound | mg/kg | value | % | 1) | % | 2) | value | % | 1) | % | 2) |
|---|---|---|---|---|---|---|---|---|---|---|---|
| Etofibrate | 220 | 72.44 | 95.12 | +31.3 | 123.5* | 29.8 | 77.68 | 78.7* | +1.3 | 176.64 | +124.4 |
| Clofibrate | 150 | 72.08 | 98.6 | +36.8 | 151.9* | 54.1 | 90.72 | 87.1* | −4.0 | 219.8 | +152.3 |
| Nicotinic acid | 80 | | | | | | | | | | |

1) percentage change from initial value
2) percentage change from value after 2 weeks
* Figures determined from plotted mass-graduation; slight deviations possible Apart from the above-mentioned improved activity, the following advantages are exhibited by the salts in accordance with the invention:

a. the salts are almost insoluble in water, but dissolve very readily in lipoid solvents such as acetone, alcohols, acetic esters etc.,
b. the salts are odorless, almost tasteless and do not cause any irritation of the mucous membranes, and
c. the salts also have a good anti-thrombotic effect and in particular a peripheral vasodilatory effect.

Their anti-lipemic effect in conjunction with the peripheral dilatory effect renders the salts of the invention suitable for the treatment of metabolic illnesses involving high lipid values, and particularly illnesses involving high cholesterol values which represent a decisive risk factor in the occurrence of arteriosclerosis and peripheral vascular sclerosis.

The compounds of the invention are produced using known methods, and their preparation is described in the following Examples:

EXAMPLE 1

7.36 g (0.02 mol) of cizzarizine and 4.30 g (0.02 mol) of clofibrinic acid were dissolved in 30 ml of isopropanol and heated to reflux temperature; the mixture was then filtered while hot. The filtrate, after standing over-night at room temperature, the crystals which formed were drawn off by suction and washed with 5 ml of isopropanol.

9.8 g (84.6% of theory) of cinnarizine clofibrinate were obtained as a colorless crystal having a melting point (M.P.) of 109.6° C.

The reaction was carried out in ethanol as the solvent and provided 6.6g (56.7% of theory) of cinnarizine clofibrinate as colorless needles having a M.P. of 109.8° C.

Determination of the cinnarizine and clofibrinate contents by potentiometric titration gave the following values:

titration with 0.1 N HCl O$_4$: 100.6% cinnarizine
titration with 0.1 N NaOH: 99.8% clofibrinic acid

EXAMPLE 2

4.05 g (0.01 mol) of cinnarizine hydrochloride were dissolved in water and mixed by stirring with a separately prepared solution of 2.37 (0.01 mol) of sodium salt of clofibrinic acid in water.

The resulting crystals were drawn off by suction, washed with water and after drying were recrystallized from a little ethanol.

4.56 g (78.2% of theory) of cinnarizine clofibrinate were obtained in the form of colorless crystals having a M.P. of 109.7° C.

Using the method of preparation described in Example 1, the following further salts were produced, using the appropriate starting materials, by concentrating the reaction solution by evaporation.

EXAMPLE 3

Cinnarizine-p-chlorophenoxypropionate, a yellowish viscous oil.
Content: (cinnarizine 101.1% of theory/p-chlorophenoxypropionic acid 99.6% of theory)

EXAMPLE 4

Cinnarizine-p-chlorophenoxyacetate, a colorless viscous oil.
Content: (cinnarizine 102.2% of theory/p-chlorophenoxyacetic acid 100.3% of theory)

EXAMPLE 5

Cinnarizine-bis-(p-chlorophenoxy) acetate, a yellowish viscous oil.
Content: (cinnarizine 99.6% of theory/bis-(p-chlorophenoxyacetic acid 100.9% of theory)

The viscous compounds described in connection with Examples 3 and 4 could not be obtained in pure form by suitable crystallization since according to the solvent used, the crystal obtained was contaminated to varying extents by cinnarizine, i.e., determination of the contents of the viscous raw products gave closely corresponding values in contrast to the crystals.

The medicaments in accordance with the invention contain one or more phenoxyalkylcarboxylic acid salts having the general formula I, optionally in combination with further phenoxyalkylcarboxylic acid derivatives.

The medicaments are preferably administered orally, e.g. in the form of capsules, tablets or lozenges which may also contain the usual pharmaceutical carrier substances and adjuvants.

The normal adjuvants for tablets and lozenges are:
starch, lactose, talc, magnesium stearate and calcium stearate, micro-fine cellulose and aerosil;
for films for coating tablets:
polymeric methacrylate lacquer in a form which is soluble or insoluble in gastric juices;
for capsules:
starch, lactose, talc, micro-fine cellulose;
for rectal capsules:
vegetable oils and hydrated vegetable oils; emulsifiers and bodying agents (waxes, soya lecithin) for preventing sedimentation.

The compounds in accordance with the invention are administered, depending upon the particular case, in daily oral or rectal doses of 300 to 1200 mg, preferably 400 to 800 mg, in the usual pharmaceutical forms.

Where the compounds of the invention are combined with other phenoxyalkylcarboxylic acid derivatives for the treatment of milder cases of hyperlipemia, the use of clofibrate and clofibrinic acid is particularly preferred.

The following Examples are given for explanatory purposes, and the invention is not limited thereto:

EXAMPLE 6

Tablets

| Compound of Example 1 | | 150.0 mg |
|---|---|---|
| Binding agents: | micro-fine cellulose | 100.0 mg |
| | lactose | 50.0 mg |
| | potato starch | 60.0 mg |
| | talc | 14.0 mg |
| | magnesium stearate | 6.0 mg |

EXAMPLE 7

Capsules

| Compound of Example 1 | | 150.0 mg |
|---|---|---|
| Binding agents: | corn starch | 30.0 mg |
| | lactose | 60.0 mg |

EXAMPLE 8

Capsules

| Compound of Example 1 | | 150.0 mg |
|---|---|---|
| Binding agents: | wax | 40.0 mg |
| | soya lecithin | 10.0 mg |
| | vegetable oils | 10.0 mg |
| | aerosil | 80.0 mg |

Composition of shell of the capsule:
gelatin, glycerine, sorbite, ethyl parabene and propyl parabene, colorant.

EXAMPLE 9

Rectal capsules

| Compound of Example 3 | | 200.0 mg |
|---|---|---|
| Binding agents: | Cremophor* EL | 30.0 mg |
| | soya lecithin | 25.0 mg |
| | wax mixture | 180.0 mg |
| | vegetable oil | 360.0 mg |
| | partially hydrated vegetable oils | 121.0 mg |

Gelatin shell: gelatin, glycerine, ethyl parabene and propyl parabene, colorant.
Coating: polyclycol 20,000, glycerine mono-oleate and di-oleate, polyvinyl acetate.

We claim:

1. Phenoxyalkylcarboxylic acid derivatives of 1-cinnamyl-4-diphenylmethylpiperazine (cinnarizine) having the general formula:

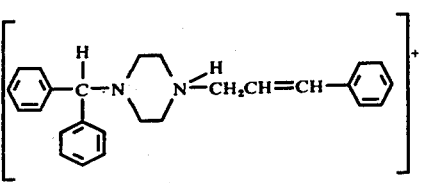

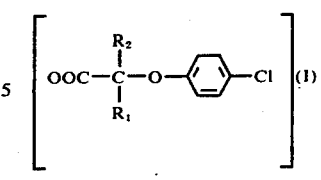

wherein
$R_1$ is a hydrogen atom, an alkyl group of from 1 to 4 carbon atoms or a p-chlorophenoxy group, and
$R_2$ is a hydrogen atom or an alkyl group of from 1 to 4 carbon atoms.

2. A process of preparing phenoxyalkylcarboxylic acid derivatives of 1-cinnamyl-4-diphenylmethylpiperazine (cinnarizine) having the general formula:

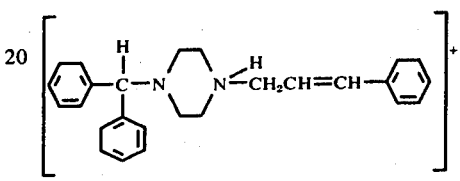

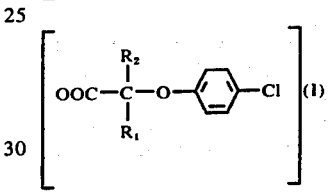

wherein
$R_1$ is a hydrogen atom, an alkyl group of from 1 to 4 carbon atoms or a p-chlorophenoxy group, and
$R_2$ is a hydrogen atom or an alkyl group of from 1 to 4 carbon atoms which comprises reacting phenoxyalkylcarboxylic acid, a reactive derivative thereof wherein $R_1$ is hydrogen alkyl of from 1 to 4 carbon atoms or p-chlorophenoxy and $R_2$ is hydrogen or alkyl of from 1 to 4 carbon atoms with cinnarizine or a reactive derivative thereof in equimolar quantities in a suitable solvent.

3. Medicament, which comprises an antihypercholesteremic amount of one or more compounds of the formula:

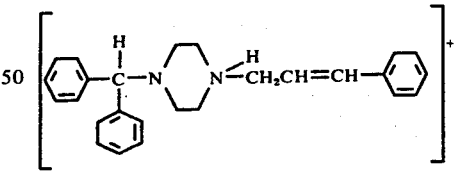

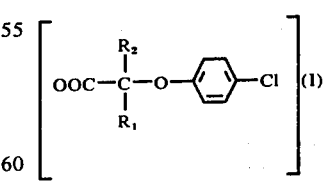

wherein
$R_1$ is a hydrogen atom, an alkyl group of from 1 to 4 carbon atoms or a p-chlorophenoxy group, and
$R_2$ is a hydrogen atom or an alkyl group of from 1 to 4 carbon atoms together with pharmaceutical acceptable carriers or adjuvants.

* * * * *